(12) United States Patent
Rhodes et al.

(10) Patent No.: US 10,874,758 B2
(45) Date of Patent: Dec. 29, 2020

(54) SYSTEM AND METHOD FOR STORAGE OF A MEDICAL DEVICE

(71) Applicant: Ethicon, Inc., Somerville, NJ (US)

(72) Inventors: Samuel Jackson Rhodes, Los Angeles, CA (US); Natalie R. Holger, Mountain View, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 212 days.

(21) Appl. No.: 15/854,378

(22) Filed: Dec. 26, 2017

(65) Prior Publication Data

US 2019/0192713 A1 Jun. 27, 2019

(51) Int. Cl.

| | |
|---|---|
| *A61L 2/24* | (2006.01) |
| *A61L 2/26* | (2006.01) |
| *A61B 50/30* | (2016.01) |
| *A61B 90/70* | (2016.01) |
| *A61L 2/28* | (2006.01) |
| *A61B 50/13* | (2016.01) |
| *A61B 50/36* | (2016.01) |
| *A61L 2/18* | (2006.01) |
| *A61B 50/10* | (2016.01) |
| *A61B 50/18* | (2016.01) |

(52) U.S. Cl.
CPC ................ *A61L 2/24* (2013.01); *A61B 50/10* (2016.02); *A61B 50/13* (2016.02); *A61B 50/18* (2016.02); *A61B 50/30* (2016.02); *A61B 50/36* (2016.02); *A61B 90/70* (2016.02); *A61L 2/18* (2013.01); *A61L 2/26* (2013.01); *A61L 2/28* (2013.01); *A61B 2050/105* (2016.02); *A61B 2050/3008* (2016.02); *A61L 2202/14* (2013.01); *A61L 2202/17* (2013.01); *A61L 2202/182* (2013.01); *A61L 2202/24* (2013.01)

(58) Field of Classification Search
CPC ..... A61L 2/18; A61L 2/24; A61L 2/26; A61L 2/28; A61B 50/10; A61B 50/13; A61B 50/18; A61B 50/30; A61B 50/36
See application file for complete search history.

(56) References Cited

U.S. PATENT DOCUMENTS

| | | | |
|---|---|---|---|
| 6,663,202 B2 | 12/2003 | Spann | |
| 7,055,833 B2 | 6/2006 | Wixted et al. | |
| 8,454,901 B1 * | 6/2013 | Snyder, III | A61L 2/07 422/26 |
| 10,086,100 B1 * | 10/2018 | Mauzerall | A61L 2/26 |

(Continued)

OTHER PUBLICATIONS

Custom Endoscopy Carts, accessed at https://www.phswest.com/products/endoscopy-carts/?gclid . . . , PHS West, Inc., 2018, 10 pages.

(Continued)

*Primary Examiner* — Sean E Conley
(74) *Attorney, Agent, or Firm* — K&L Gates LLP (57) ABSTRACT

A storage apparatus and methods for storing medical devices are provided. A storage apparatus comprises a first container having a first cavity configured to receive a first medical device, such as an endoscope, and a second container having a second cavity configured to receive a supply kit for the first medical device. The second container is positioned proximal to the first container within the storage apparatus.

10 Claims, 10 Drawing Sheets

(56) References Cited

U.S. PATENT DOCUMENTS

| | | | | |
|---|---|---|---|---|
| 2004/0101456 A1* | 5/2004 | Kuroshima | ............... | A61L 2/07 422/297 |
| 2005/0212239 A1* | 9/2005 | Carter | ....................... | A61L 2/24 280/47.35 |
| 2008/0087231 A1* | 4/2008 | Gabriel | .................. | A01K 1/031 119/455 |
| 2014/0069841 A1* | 3/2014 | Pizzato | .................. | A61F 17/00 206/570 |

OTHER PUBLICATIONS

Endoscope Trolley—All Medical Device Manufacturers, accessed at http://www.medicalexpo.com/medical-manufacturer/endoscope-trolley-3272.html, Medical Expo, 2018, 23 pages.

\* cited by examiner

SYSTEM AND METHOD FOR STORAGE OF A MEDICAL DEVICE

FIELD OF THE INVENTION

The present disclosure relates to a storage apparatus and methods for storing medical devices.

BACKGROUND

Various medical devices are employed for procedures in the medical field. These devices are as varied as the treatments themselves. As such, proper care of these devices is critical for the proper corresponding treatment of the patient.

After a medical device, such as an endoscope, is used, the medical device is cleaned, disinfected, and/or sterilized in order to prepare the medical device for its next use. For example, shortly after the use, the medical device may undergo a preliminary cleaning, disinfecting, and/or sterilizing procedure near the location the medical device was used. After the preliminary procedure is executed, the medical device may be subjected to subsequent, more rigorous, cleaning, disinfecting, and/or sterilization in order to prepared the medical device for its next use. While the medical device is dirty and/or being cleaned, disinfected, and/or sterilized, the medical device is typically unavailable for use, resulting in downtime of the medical device.

SUMMARY

In one aspect, the present disclosure provides a sterilization storage apparatus. More specifically, the apparatus comprises a first container having a first cavity configured to receive a first endoscope and a second container having a second cavity configured to receive a supply kit for the first endoscope. The second container is positioned proximal to the first container within the storage apparatus.

In another aspect, a sterilization storage apparatus is provided. More specifically, the apparatus comprises a first container having a first cavity configured to receive a first endoscope and a second container having a second cavity configured to receive a supply kit for the first endoscope. The second container is positioned proximal to the first container within the storage apparatus. The supply kit includes at least one of a rag, a cloth, a paper product, a brush, a sponge, a spray device, a valve, and a fitting. A visual indicator is associated with at least one of the first container and the second container and is configured to indicate a state of the endoscope.

In another aspect, a method is provided for storing sterilization equipment. More specifically, an endoscope is stored in a first container in a storage apparatus. A supply kit is stored in a second container in the storage apparatus. The second container is positioned proximal to the first container.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description taken in conjunction with the accompanying drawings, wherein.

Corresponding reference characters indicate corresponding parts throughout the several views. The exemplifications set out herein illustrate certain embodiments, in one form, and such exemplifications are not to be construed as limiting the scope of the embodiments in any manner.

DETAILED DESCRIPTION

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification such that amending to expressly recite any such sub-ranges would comply with the requirements of 35 U.S.C. § 112 and 35 U.S.C. § 132(a).

Various medical devices are employed for procedures in the medical field. For example, when the medical device is an endoscope, these devices are commonly employed to examine the interior of a hollow organ or cavity of the body. As such, the medical device is typically in a sterile state prior to being use on a patient. During or after use of the medical device, the procedure or medical device may require the use of a cleaning, disinfecting, and/or sterilizing procedure that may include the use of a cleaning supply, such as but not limited to, a rag, a cloth, a paper product, a brush, a sponge, a spray device, a valve, and a fitting. Inefficiently managing and/or finding the correct supplies to support the cleaning procedure can consume more time than needed for the procedure. Moreover, incorrect storage of supplies can lead to inefficient use of space and cross-contamination of a sterile medical device from a non-sterile medical device.

Efficient management of space can limit, and in certain examples prevent, cross-contamination and facilitate rapid location of a supply and/or a medical device. Thus, a sterilization storage apparatus and a method are provided for efficiently storing a supply kit proximal to a medical device, such as an endoscope.

Figure 1:
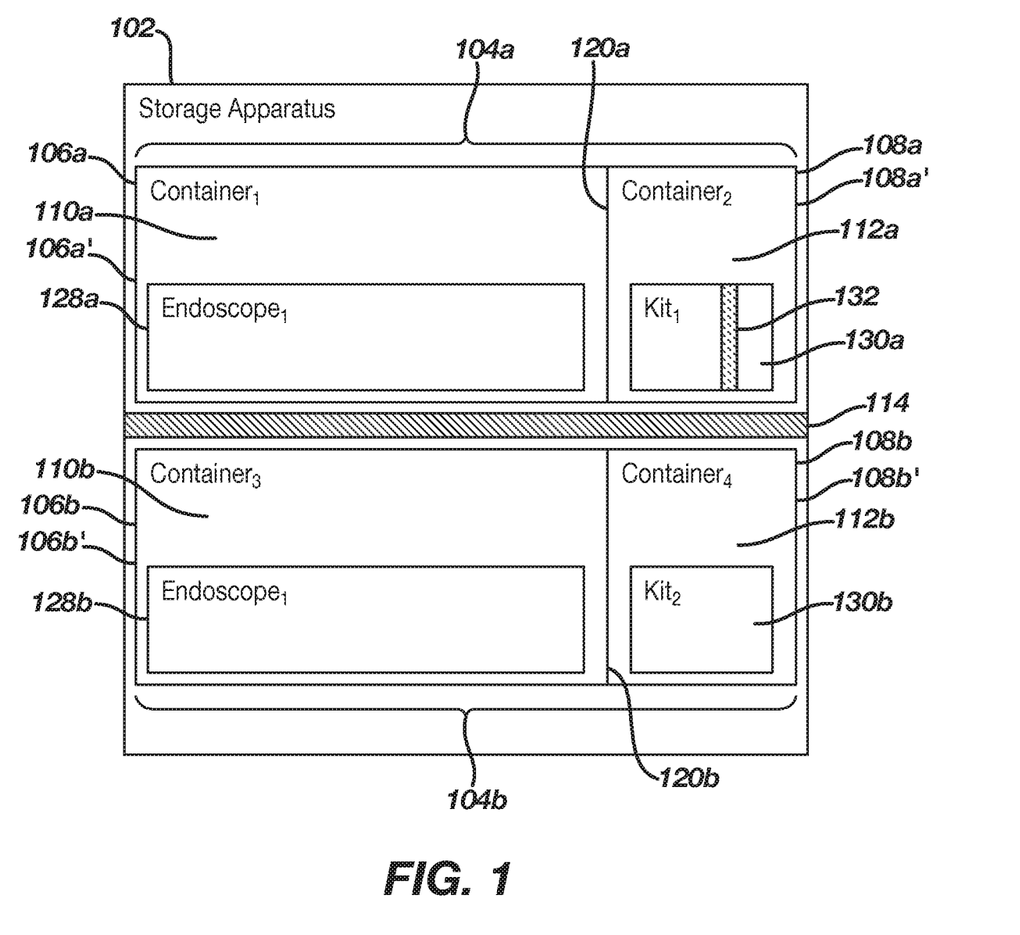
FIG. 1 is illustrates a storage apparatus for an endoscope and a supply kit.

Referring to FIG. 1, the figure illustrates a storage apparatus 102 for an endoscope and a supply kit. As shown, the storage apparatus 102 is provided with a first unit 104a having a first container 106a and a second container 108a positioned proximal to the first container 106a. In certain examples, first and second containers, 106a and 108a, respectively, may have housings 106a' and 108a', respectively, that have a shared or common sidewall 120a. In other examples, first and second containers, 106a and 108a, may each be completely enclosed to themselves such that the housings 106a' and 108a' forming each adjoining container 106a and 108a, respectively, may each have separate sidewalls that result in double-walled separation. In certain examples, the first and second containers, 106a and 108a, respectively, can be formed from a single continuous material, such as a stamped wall.

The first container 106a has a cavity 110a which can be configured to receive an object, such as an endoscope 128a. In certain examples, the endoscope 128a can be positioned completely within the cavity 110a. Similarly, the second container 108a has a cavity 112a which can be configured to receive an object such as a supply kit 130a. In certain examples, the supply kit can be positioned completely within the cavity 112a.

The supply kit 130a may support a cleaning, disinfecting, and/or sterilizing procedure during a patient procedure or for a medical device, such as the endoscope 128a. For example, the supply kit 130a may comprise supply equipment, such as, but not limited to, a rag, a cloth, a paper product, a brush, a sponge, a spray device, a valve, and a fitting. The supply may be used in the cleaning, disinfecting, and/or sterilizing procedure. In one example, the supply kit 130a may contain a spray device, such as a spray bottle, containing a cleaning solution, and a cloth to wipe down the endoscope 128a. The positioning of the first and second containers, 106a and 108a, respectively, can enable storage of the endoscope 128a proximal to the supply kit 130a. The proximal location can enhance efficiency in locating a supply for supporting cleaning, disinfecting, and/or sterilization of the endoscope 128a. Accordingly, the enhanced efficiency increases availability of the endoscope 128a in a given time period.

The supply kit 130a may be, but is not limited to, a re-usable or disposable kit. For example, a re-usable supply kit may comprise, but is not limited to, supplies for multiple cleaning procedures. A disposable supply kit may comprise, for example, a limited amount of supplies and a paper box enclosing the limited amount of supplies. When the supply kit 1340a is a disposable supply kit, the supply kit 130a may be sized to receive a discarded material from a cleaning, disinfecting, and/or sterilizing procedure involving the medical procedure or the medical device, such as the endoscope 128a. For example, when the supply kit 130a comprises a paper box the supply kit 130a enclosing the supplies may be sized to receive the discarded material and have a closeable lid. Accordingly, the proximal location of the supply kit 130a to the endoscope 128a may facilitate rapid disposal of a discarded material such as a used supply.

In certain examples, the supply kit 130a may comprise a tamper evident seal 132 which can indicate the state of the supply kit 130a, such as whether the supply kit 130a is sterile or non-sterile and/or used or unused. For example, the tamper evident seal 132 can be broken upon accessing a supply within the supply kit 130a. For example, when broken, the tamper evident seal 132 can indicate the supply kit 130a was used and/or accessed and thus, it can be readily determined that the supply kit is non-sterile.

In certain examples, the storage apparatus 102 may be provided with a plurality of units. For example, the storage apparatus 102 may have a second unit 104b. The units 104a-b can be arranged in a suitable configuration, such as a stacked configuration, wherein the first unit 104a positioned on top of the second unit 104b as illustrated in FIG. 1. In certain examples, the second unit 104b can be positioned on top of the first unit 104a. The second unit 104b may comprise a third container 106b and a fourth container 108b which can be positioned proximal to the third container 106b. In certain examples, the third and fourth containers, 106b and 108b, may have housings 106b' and 108b', respectively, that have a shared or common sidewall 120b. In other examples, third and fourth containers, 106b and 108b, may each be completely enclosed to themselves such that the housings 106b' and 108b' forming each adjoining container 106b and 108b, respectively, may each have separate sidewalls that result in double-walled separation. Accordingly, as illustrated, the storage apparatus 102 can be configured with multiple units.

In certain examples, each unit 104a-b may have a cavity which can receive both at least one medical device, such as an endoscope, and a supply kit. In certain examples, each unit 104a-b may have more than two cavities. In certain examples, the first container 106a can be positioned above the second container 108a such that the containers, 106a and 106b, are configured in a stacked orientation. Thus, the quantity and positioning of the cavities and/or containers is for illustration purposes only, and the storage apparatus 102 may be configured with a different quantity of containers and/or cavities and/or arranged in a different configuration than illustrated.

Similar to the first container 106a, the third container 106b has a cavity 110b which can be configured to receive an object such as a medical device, such as, for example, an endoscope 128b. Similar to the second container 108a, the fourth container 108b may have a cavity 112b which can be configured to receive an object such as a supply kit 130b. The positioning of the first and second containers, 106b and 108b, respectively, can enable storage of the medical device such as the endoscope 128b proximal to the supply kit 130b. The proximal location can enhance efficiency in locating a supply for supporting cleaning, disinfecting, and/or sterilization during the medical procedure or the endoscope 128b. Accordingly, the enhanced efficiency increases availability of the endoscope 128b in a given time period.

As illustrated, a divider 114 can be positioned within the storage apparatus 102 and between the first unit 104a and the second unit 104b. The divider 114 can separate a "clean" unit, such as a sterilized unit, a processed unit, a disinfected unit, a cleaned unit, and the like, from an "unclean" or a "dirty" unit, such as a non-sterilized unit, a non-processed unit, a non-disinfected unit, a unclean unit, and the like The divider 114 optionally provides a physical barrier (e.g., a seal) between the units 104a-b such that cross-contamination between the units 104a-b can be limited, substantially reduced, and, in certain examples, prevented. For example, in one example, one of the first unit 104a and the second unit 104b may be a dirty unit while the other unit is a clean unit. In this example, the dirty unit can be prevented from contaminating the clean unit with a foreign body (e.g., a fluid, a particle, a living organism, and the like) by the divider 114. Additionally, there may be a plurality of dividers positioned within the storage apparatus 102. In certain examples, the divider 114 may comprise an impermeable material, such as, but not limited to, a plastic material to assist in reducing or preventing cross-contamination between clean and unclean units. The position, quantity and type of divider(s) shown are for illustration purposes only and should not be considered limiting. Accordingly, the divider 114 enables simultaneous storage of dirty and clean units within the same storage apparatus 102.

Figure 2A:
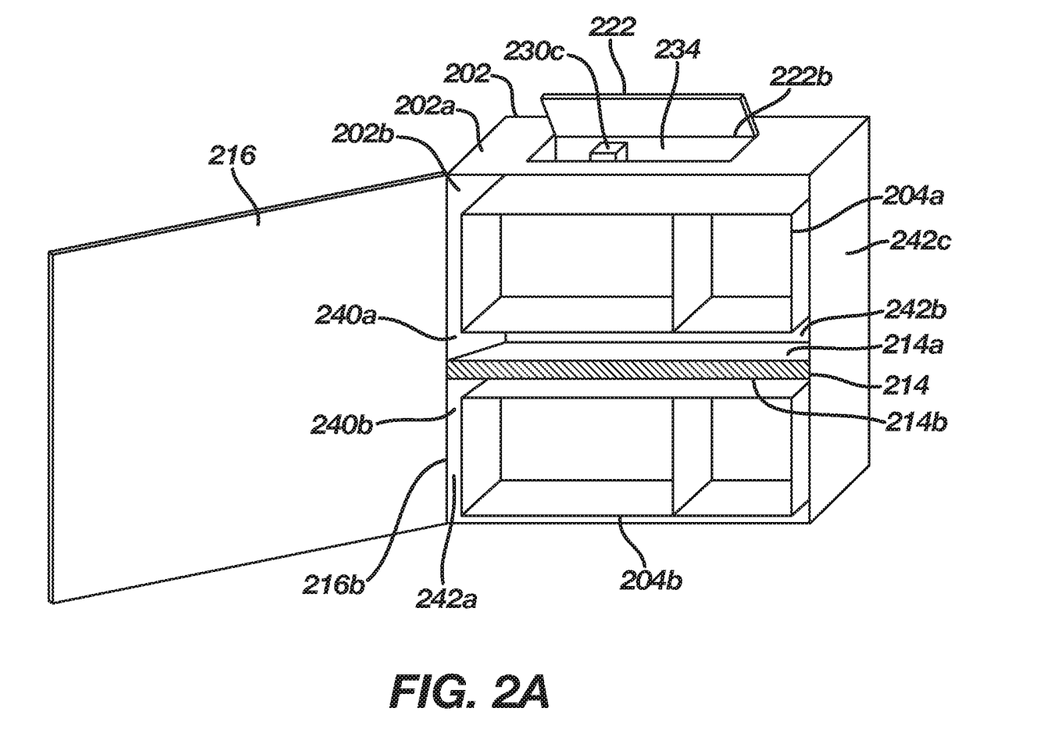
FIG. 2A is a perspective view of a storage apparatus with multiple units and a door in an open position.

Referring to FIG. 2A, the figure illustrates a storage apparatus 202 with multiple units and a door in an open position. As illustrated, the storage apparatus 202 has a housing 202a and an interior cavity 202b. A first unit 204a and a second unit 204b are positioned within the interior cavity 202b. A door 216 can be operatively coupled to the housing 202a and can limit and enable access to the units, 204a-b. For example, when the door 216 is in an open positioned, as illustrated in FIG. 2A, an operator can have unrestricted physical access to the units 204a-b, and the interior cavity 202b may be subject to environmental contamination by a foreign body such as a fluid, a particle (e.g., dirt, dust, etc.), a living organism (e.g., bacteria, virus, etc.), etc. Whereas, when the door 216 is in a closed position, as illustrated in FIG. 2B, an operator has restricted physical access to the units 204a-b and environmental contamination can be limited, and in certain examples, prevented, from entering the interior cavity 202b.

Figure 4:
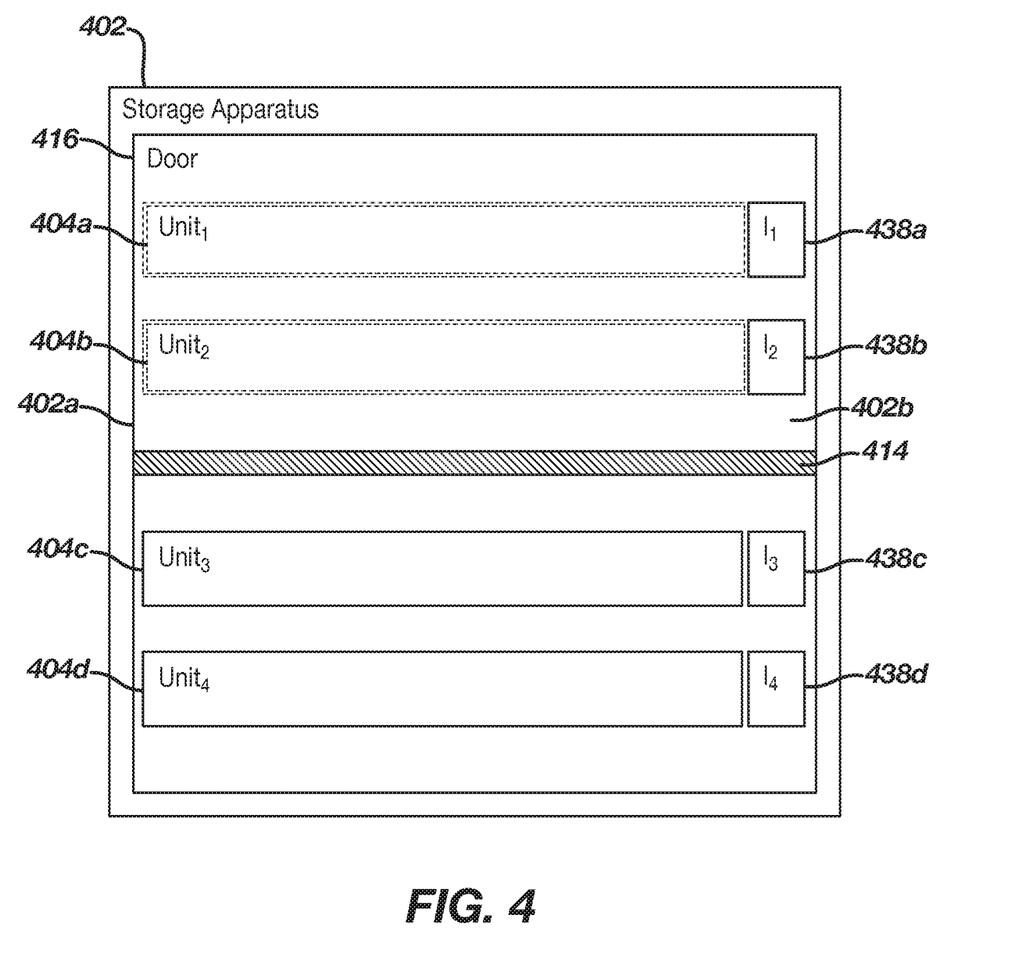
FIG. 4 is a plan view of a storage apparatus with a visual indicator to communicate a state of a unit.

The door 216 may have, but is not limited to, a transparent configuration, an opaque configuration, and various degrees thereof. In a transparent configuration, an operator may view the units 204a-b while the door 216 is in the closed positioned. FIG. 4, further described herein, provides an example of a storage apparatus 402 with a transparent door 416. Referring again to FIG. 2B, in examples where the door 216 has an opaque configuration, the door 216 limits an operator's view of the units 204a-b while the door 216 is in the closed position, relative to the transparent configuration. In certain examples, the door 216 may comprise frosted glass. Accordingly, the door 216 can be provided to limited physical access and/or limit environmental contamination of the units 204a-b.

Figure 2B:
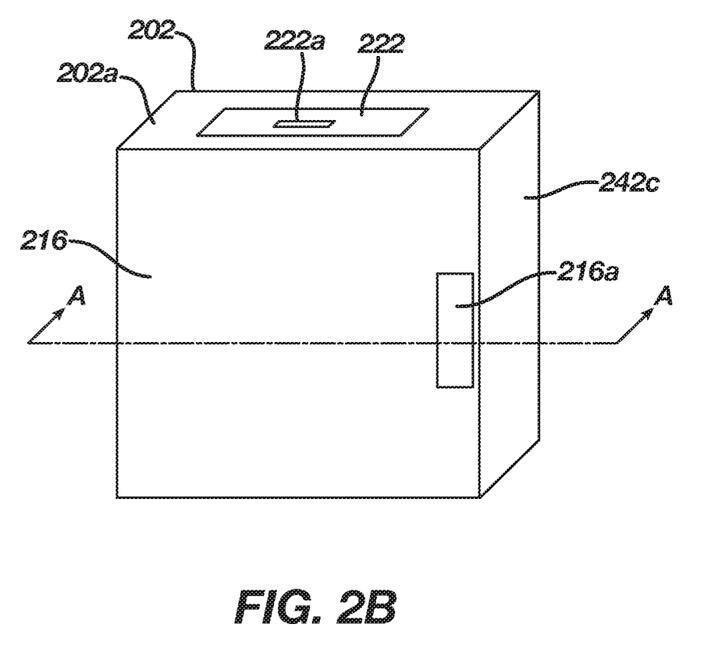
FIG. 2B is a perspective view of a storage apparatus with multiple units and a door in a closed position.

As illustrated in FIGS. 2A-2B, a divider 214 enables separation of the first and second units, 204a and 204b, respectively. The separation limits, and in certain examples prevents, cross-contamination from a dirty unit to a clean unit. For example, the divider 214 limits, and in certain examples, prevents, exchange of at least one of: a fluid, a particle, a living organism, and the like between a first area 240a of the interior cavity 202b adjacent to a first side 214a of the divider 214 and a second area 240b of the interior cavity 202b adjacent to a second side 214b of the divider 214.

Figure 2C:
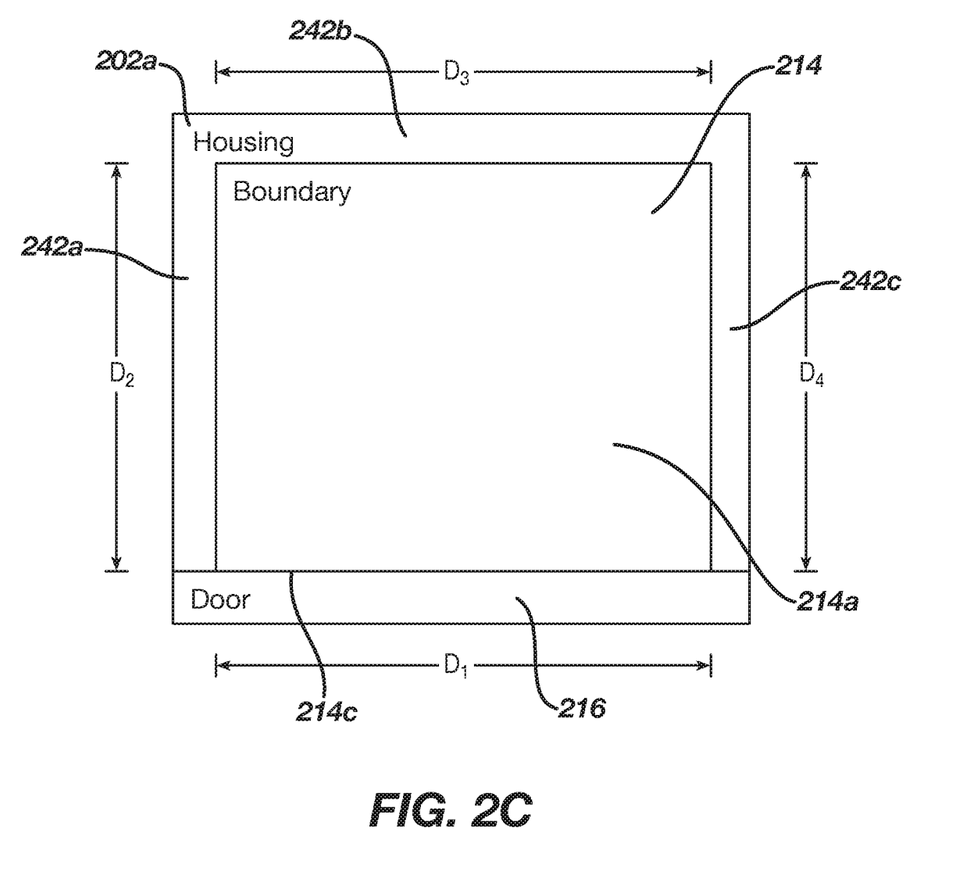
FIG. 2C is a cross-sectional view cut along line A-A of the storage apparatus of FIG. 2B.

In certain examples, when the door 216 is in the closed position, the door 216 engages the divider 214 to form a good enclosure and, in some examples, a complete seal. Referring to FIG. 2C, a cross-sectional view cut along line A-A of the storage apparatus of FIG. 2B is provided. As illustrated, in certain examples, the divider 214 creates a physical barrier (e.g., seal) between the first area 240a and the second area 240b by physically contacting a first wall 242a of the housing 202a, a second wall 242b of the housing 202a, a third wall 242c of the housing 202a, and the door 216 when the door 216 is in the closed position (FIGS. 2B-C). More specifically, the divider 214 maintains physical contact with the door 216 along a first dimension $D_1$ of the divider 214 in order to create a seal therewith; the divider 214 maintains physical contact with the first wall 242a along a second dimension $D_2$ of the divider 214 in order to create a seal therewith; the divider 214 maintains physical contact with the second wall 242b along a third dimension $D_3$ of the divider 214 in order to create a seal therewith; and the divider 214 maintains physical contact with the third wall 242c along a fourth dimension $D_4$ of the divider 214 in order to create a seal therewith. The shape of the divider 214, the walls 242a-c, and the door 216 is for illustration purposes only and the divider 214, the walls 242a-c, and the door 216 may be any shape. Regardless of the shape, in certain examples, a perimeter 214c of the divider 214 can be configured with a contour such that the perimeter 214c is in continuous physical contact with the housing 202a and the door 216, in the closed position, such that cross-contamination between the first area 240a and second area 240b can be limited, and in certain examples, prevented. Accordingly, the positioning and configuration of the divider 214 can limit cross-contamination from a dirty unit to a clean unit.

The door 216 can be configured to change position, such as from the open position to the closed position, by rotating around a pivot 216b, such as, but not limited to, a hinge. The door 216 has a handle 216a which can be configured to receive a force in order to change the position of the door 216 and facilitate rotation around the pivot 216b. For example, a force applied to the handle 216a can move the door 216 around the pivot 216b in a direction of the force subject to a physical constraint of the housing 202a such as physical contact between the housing 202a and the door 216 and a physical constraint of the pivot 216b. Accordingly, the door 216 can be provided with the pivot 216b to facilitate position changes of the door 216.

As illustrated in FIG. 2A-2B, in certain examples, the housing 202a may be provided with multiple doors, for example, the door 216 and a door 222 which can both limit and enable access to a cavity 234. The cavity 234 can be configured to receive a supply kit 230c. For example, when the door 222 is in an open position, as illustrated in FIG. 2A, the supply kit 230c can be physically accessible to an operator. Whereas when the door 222 is in a closed position, as illustrated in FIG. 2B, the operator can have limited access to the supply kit 230c. The door 222 can be configured to change position, such as from the open position to the closed position, by rotating around a pivot 222b, such as, but not limited to, a hinge. The door 222 can have a handle 222a which can be configured to receive a force in order to change the position of the door 222 and facilitate rotation around the pivot 222b. For example, a force applied to the handle 222a can move the door 222 around the pivot 222b in a direction of the force subject to a physical constraint of the housing 202a such as physical contact between the housing 202a and the door 222 and a physical constraint of the pivot 222b. Accordingly, the door 222 can be provided with the pivot 222b to facilitate position changes of the door 222.

Figure 3A:
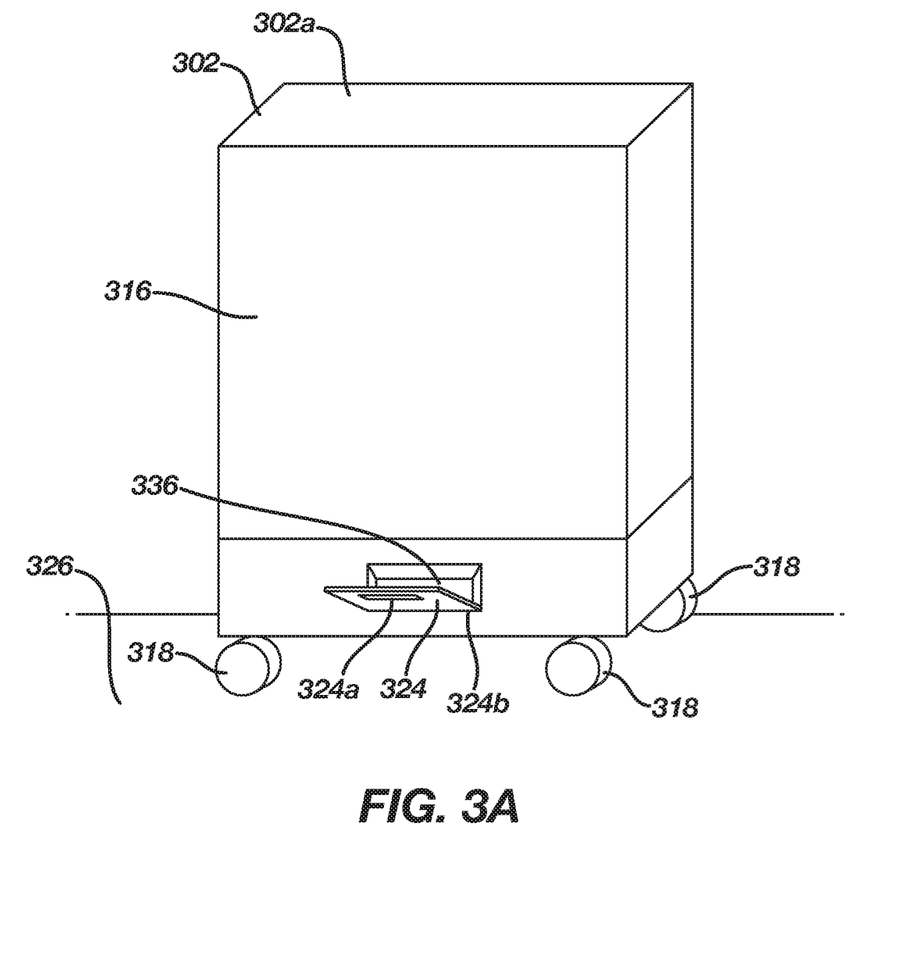
FIG. 3A is a perspective view of a storage apparatus with multiple units and a door for receiving an object in an open position.
Figure 3B:
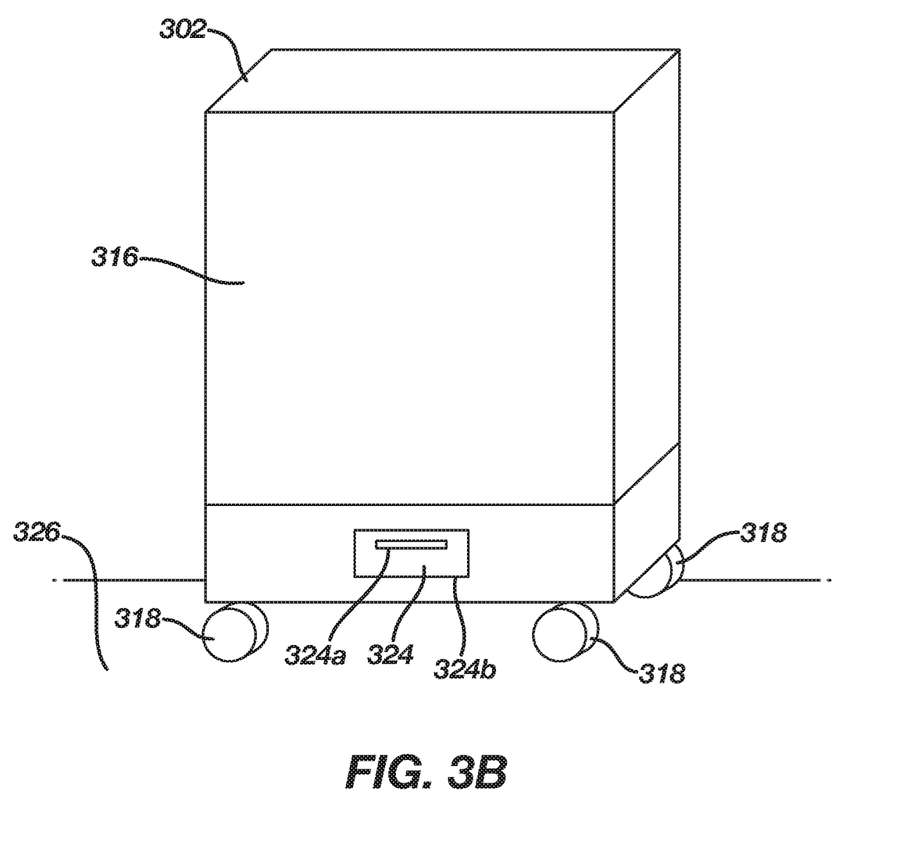
FIG. 3B is a perspective view of a storage apparatus with multiple units and a door for receiving an object in a closed position.

FIG. 3A illustrates a storage apparatus 302 with multiple units and a door for receiving an object in an open position. As illustrated, the storage apparatus 302 has a housing 302a with a door 316 and a door 324 which can limit and enable access to a cavity 336 which can receive an object, such as used supply or processing material. For example, when the door 324 is in an open position, as illustrated in FIG. 3A, the cavity 336 can receive the object for storage. In certain examples, the receipt of the object includes positioning the object entirely within the cavity 336. Whereas when the door 324 is in a closed position, as illustrated in FIG. 3B, the cavity 336 may not be able to actively receive the object and the door 324 can restrict access to the cavity 336. However, an object may be contained within the cavity 336 while the door 324 is in the open positon and in the closed position.

The door 324 can be configured to change position from the closed position to the open position by rotating around a pivot 324b, such as, but not limited to, a hinge. The door 324 can have a handle 324a which can be configured to receive a force in order to change the position of the door 324 and facilitate rotation around the pivot 324b. For example, a force applied to the handle 324a can move the door 324 around the pivot 324b in a direction of the force subject to a physical constraint of the housing 302a such as physical contact between the housing 302a and the door 324 and a physical constraint of the pivot 324b. In certain examples, the handle 324a can be configured to engage a shoe and/or a foot of an operator. Accordingly, the door 324 can be provided with the pivot 324b to enable position changes.

In certain examples, a transport member 318 can be operatively coupled to the housing 302a which can enhance the portability of the storage apparatus 302. For example, the transport member 318 may be, but is not limited to, a wheel, a caster, a skate, a roller, and a combination thereof. In certain examples, there can be a plurality or set of transport members 318. The transport member 318 engages a secondary surface 326 and enables the storage apparatus 302 to move along the secondary surface 326 when a force is applied to the storage apparatus 302 by reducing a force of friction between the storage apparatus 302 and the secondary surface 326. Accordingly, the housing 302a can be provided with the transport member(s) 318 to enable movement of the storage apparatus 302 with respect to the second surface 326.

FIG. 4 illustrates a storage apparatus 402 with one or more visual indicators to communicate a state of a unit. In particular, the storage apparatus 402 comprises a first visual indicator 438a and in certain examples, a second visual indicator 438b, a third visual indicator 438c, and a fourth visual indicator 438d. The visual indicators 438a-d may be, but are not limited to, a light emitting diode, a fluorescent blub, an incandescent bulb, and their combinations. Each visual indicator 438a-d can be operatively coupled to a respective unit 404a-d. Namely; the first visual indicator 438a can be operatively coupled to the first unit 404a; the second visual indicator 438b can be operatively coupled to the second unit 404b; the third visual indicator 438c can be operatively coupled to the third unit 404c; and the fourth visual indicator 438d can be operatively coupled to the fourth unit 404d. The configuration of the storage apparatus 402 with the units 404a-d is for illustration purposes only and the storage apparatus 402 may be configured in a plurality of various layouts and different quantities of units.

Each visual indicator 438a-d can communicate which state the respective unit 404a-d, or subcomponent of the unit (e.g., endoscope, supply kit, etc.) is in. The state may be, but is not limited to, clean and dirty (e.g., sterile and non-sterile, processed and non-processed, disinfected and non-disinfected, cleaned and uncleaned, etc.). The visual indicators 438a-d may indicate the state of a respective unit 404a-d or subcomponent by, for example, an illumination, a partial illumination, a non-illumination, a change in intensity of illumination, a change in color of illumination, and a change in an illumination pattern (e.g., strobe, flashing, etc.). For example, illumination of a unit or a subcomponent of a unit may indicate the unit or subcomponent is a clean unit/subcomponent whereas non-illumination may indicate the unit or subcomponent is a dirty unit/subcomponent. Similarly, in certain examples, illumination of a unit or a subcomponent may indicate the unit or subcomponent is a dirty unit/subcomponent and non-illumination may indicate a unit or subcomponent is a clean unit/subcomponent. As illustrated, the first and second units, 404a-b, are illuminated to indicate the state of the respective units 404a-b as sterile and the second and third units, 404c-d are not illuminated to indicate the state of the respective units 404c-d as non-sterile.

The storage apparatus 402 has a housing 402a with a door 416 which is at least partially transparent such that at least a portion of light emitted by the visual indicators 438a-d can be visible through the door 416. In certain examples, the door 416 can be opaque and a visual signal produced by the visual indicators 438a-d can be visible to an operator when the door is in an open position. In certain examples, the visual indicators 438a-d are positioned outside of a cavity 402b of the storage apparatus 402 such that the visual indicators 438a-d are visible when the door 416 is opaque and in a closed position. Accordingly, the visual indicators 438a-d may be configured in a variety of different arrangements.

As illustrated, a divider 414 can be positioned within the storage apparatus 402 and between the second unit 404*b* and the third unit 404*c*. The divider 414 can separate a "clean" unit, such as a sterilized unit, a processed unit, a disinfected unit, a cleaned unit, and the like, from an "unclean" or a "dirty" unit, such as a non-sterilized unit, a non-processed unit, a non-disinfected unit, a unclean unit, and the like The divider 414 optionally provides a physical barrier (e.g., a seal) between the units 404*b-c* such that cross-contamination between the units 404*b-c* can be limited, substantially reduced, and, in certain examples, prevented. For example, in one example, at least one of the first unit 404*a*, the second unit 404*b*, the third unit 404*c*, and the fourth unit 404*d* may be a dirty unit while at least one of the other unit(s) is a clean unit. In this example, the dirty unit can be prevented from contaminating the clean unit with a foreign body (e.g., a fluid, a particle, a living organism, and the like) by the divider 414. Additionally, there may be a plurality of dividers positioned within the storage apparatus 402. In certain examples, the divider 414 may comprise an impermeable material, such as, but not limited to, a plastic material to assist in reducing or preventing cross-contamination between clean and unclean units. The position, quantity and type of divider(s) shown are for illustration purposes only and should not be considered limiting. Accordingly, the divider 414 enables simultaneous storage of dirty and clean units within the same storage apparatus 402.

Figure 5:
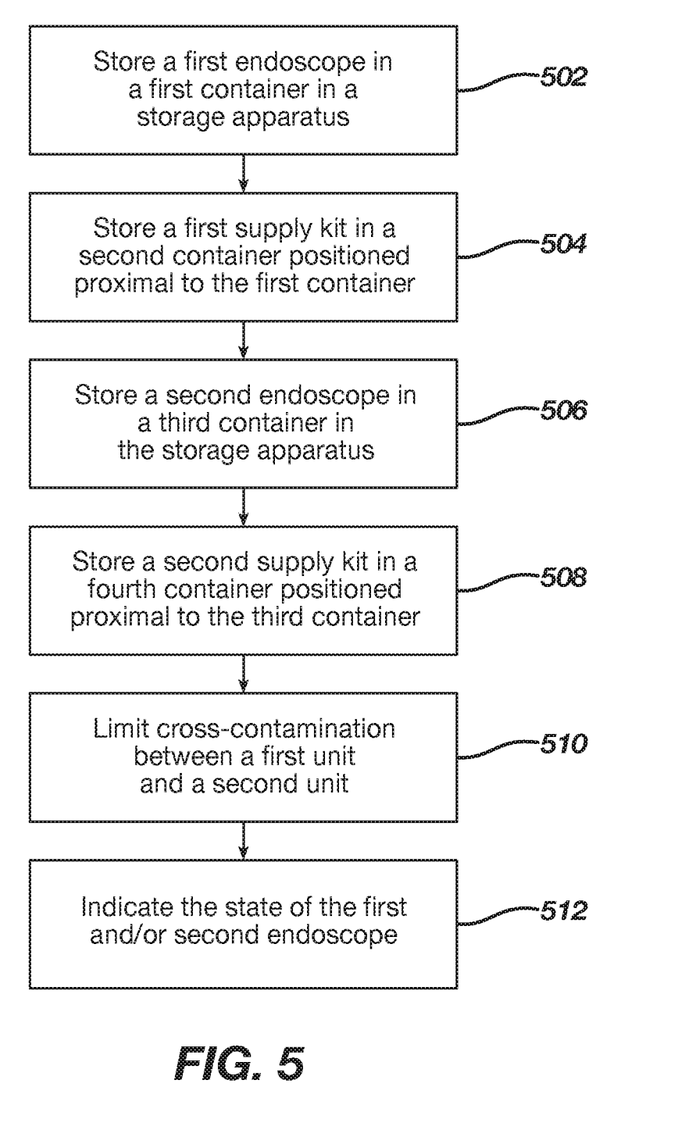
FIG. 5 is a flow chart illustrating a method for storing sterilization equipment.

Referring to FIG. 5, the figure illustrates a method for storing sterilization equipment. As illustrated, a first medical device, such as a first endoscope, is stored in a first container in a storage apparatus 502. In certain examples, storing the first endoscope includes placing the first endoscope into a cavity of the first container. A first supply kit is stored in a second container in the storage apparatus 504. The second container is positioned proximal to the first container. In certain examples, storing the first supply kit includes placing at least one of a paper box, a rag, a cloth, a paper product, a brush, a sponge, a spray device, a valve, and a fitting into a cavity of the second container. Accordingly, the proximal location of the first supply kit to the first endoscope can increase the availability of the first endoscope by rapid location of a supply for a cleaning, disinfecting, and/or sterilizing procedure, such as involving the first endoscope.

In certain examples, a second endoscope is stored in a third container in the storage apparatus 506. In certain examples, storing the second endoscope includes placing the second endoscope into a cavity of the third container. A second supply kit is stored in a fourth container in the storage apparatus 508. The fourth container is positioned proximal to the third container. In certain examples, storing the second supply kit includes placing at least one of a paper box, a rag, a cloth, a paper product, a brush, a sponge, a spray device, a valve, and a fitting into a cavity of the fourth container. In certain examples, the first supply kit and/or second supply kit is disposable. Accordingly, multiple endoscopes and supply kits may be stored in the storage apparatus.

In certain examples, cross-contamination is limited between a first unit comprising the first and second containers and a second unit comprising the third and fourth containers 510. Limiting of cross-contamination includes preparing a divider to separate the first and second units. Preparing the divider includes establishing a physical barrier (e.g., a seal) between the first unit and the second unit. For example, one of the first unit and the second unit can be dirty unit while the other unit is a clean unit, and the dirty unit is prevented from contaminating the clean unit with a foreign body by the divider. Thus, limiting cross-contamination between the units enables simultaneous storage of clean and dirty units within the same storage apparatus.

In certain examples, the state of at least one of the first endoscope and the second endoscope is indicated utilizing a visual indicator 512. For example, the state of the respective endoscope can be, but is not limited to, clean and dirty, such as, sterile and non-sterile, processed and non-processed, disinfected and non-disinfected, cleaned and uncleaned, etc. Indicating the state of the respective endoscope can include illumination of the respective endoscope utilizing the visual indicator. Indicating the state of the respective endoscope provides a visual signal that can be interpreted by an operator. Accordingly, indicating the state of the endoscope enables rapid recognition of which endoscope is ready for use (e.g., clean) and which endoscope needs to be cleaned, disinfected, and/or sterilized (e.g., dirty).

Figure 6A:
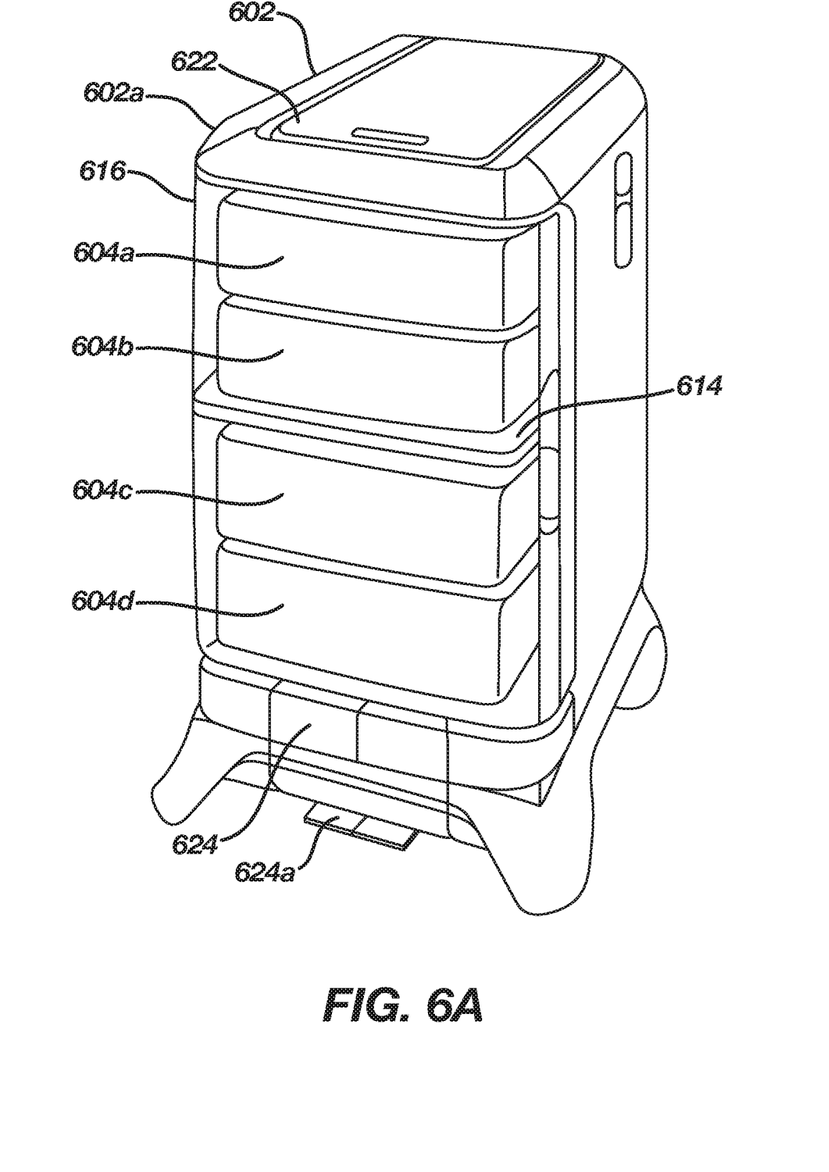
FIG. 6A. is a perspective view of a storage apparatus with a transparent door and a plurality of units.
Figure 6B:
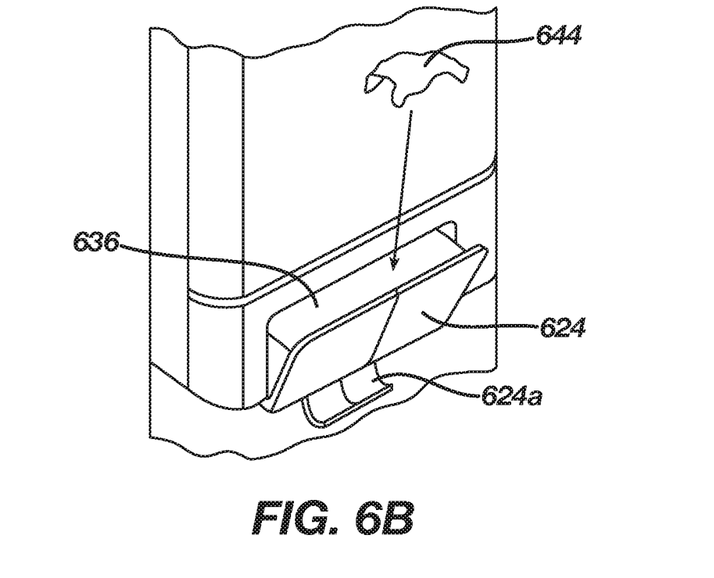
FIG. 6B is a detail view of a second door of the storage apparatus of FIG. 6A.
Figure 6C:
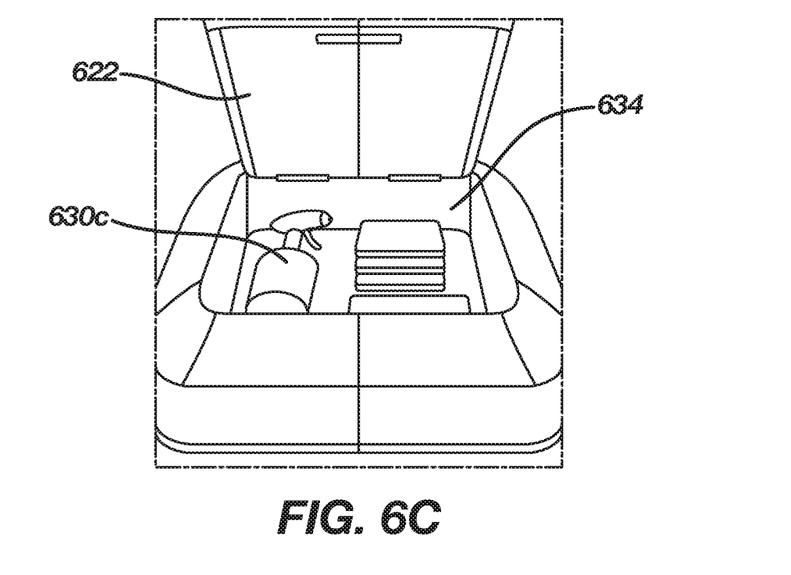
FIG. 6C is a detail view of a third door of the storage apparatus of FIG. 6C.

FIGS. 6A-C illustrate a storage apparatus 602 with a transparent door 616 and a plurality of units 604*a-d*. Each unit 604*a-d* can be configured with an endoscope position proximal to a supply kit for cleaning, disinfecting, and/or sterilizing the endoscope. In certain examples, each unit 604*a-d* can be configured to be illuminated by a visual indicator to indicate the state of the unit 604*a-d* such as, for example, clean and dirty. In certain examples, the door 616 comprises frosted glass. In certain examples, the storage apparatus 602 has a door 622 and a door 624. The door 624 can be in a close position, as illustrated in FIG. 6A, and an open position, as illustrated in FIG. 6C, wherein a cavity 634 can be exposed which has a shape for storing a supply kit 630*c*. The door 634 can have a handle 634*a* having a shape configured to receive a force from a foot and/or shoe. When the handle 643*a* receives the force, the door 634 can move from a close position, as illustrated in FIG. 6A, to an open position, as illustrated in FIG. 6B, wherein a cavity 636 can be exposed which has a shape to receive an object 644, such as an object for disposal. Thereafter, upon removal of the force or a force in a different direction, the door 634 can move from the open position back to the closed position.

A divider 614 can be positioned between the second unit 604*b* and the third unit 604*c* within the storage apparatus 602. The divider 614 can separate the first and second units, 604*a* and 604*b*, respectively from the third and fourth units, 604*c* and 604*d*, respectively. For example, the divider 616 can have a shape which physically contacts the door 616 when in a closed position and a housing 602*a* of the storage apparatus 602 in order to provide a physical barrier (e.g., seal). The physical barrier can enable storage of clean and dirty units within the storage apparatus 602 while limiting, and in certain examples preventing, cross-contamination.

In certain examples, the storage apparatus 102, 202, 302, 402, and/or 602 can be integrated with a robotic system of transport. For example, an autonomous delivery system may comprise the storage apparatus 102, 202, 302, 402, and/or 602 operatively coupled to an autonomous transport robot. The autonomous delivery system can move to/from a first location, such as an operating room, from/to a second location, such as a cleaning, disinfecting and/or sterilizing room. The autonomous delivery system can increase the efficiency in delivery of medical devices and/or supply equipment to a location since the storage apparatus 102, 202, 302, 402, and/or 602 efficiently stores medical devices and supply equipment proximal to one another and/or can simultaneously store a clean unit and a dirty unit. Thus, the autonomous delivery system can deliver a clean unit and pick up a dirty unit while limiting, and in certain examples preventing, cross-contamination. In another example, the autonomous delivery system can indicate the state of a unit within the storage apparatus 102, 202, 302, 402, and/or 602 to enable rapid recognition of which unit is ready for use (e.g., clean) upon arrival to a location, which unit is not ready for use (e.g., dirty) and, in certain examples, where an additional unit may be stored (e.g., a cavity currently without a medical device).

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more examples has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various examples and with various modifications as are suited to the particular use contemplated. It is intended that the claims submitted herewith define the overall scope.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A sterilization storage apparatus comprising:
   a first unit comprising:
   a first container having a first cavity configured to receive a first medical device;
   a second container having a second cavity configured to receive a supply kit for the first medical device, the second container is positioned proximal to the first container within the storage apparatus, wherein the first and second containers are formed from a single continuous material or have separate sidewalls that result in double-wall separation;
   a second unit comprising:
   a third container having a third cavity configured to receive a second medical device; and
   a fourth container having a fourth cavity configured to receive a second supply kit for the second medical device, the fourth container is positioned proximal to the third container within the storage apparatus;
a divider positioned between the first unit and the second unit, wherein the divider limits cross-contamination between the first and second units; and
a door configured to enable access to both the first and second units and engage the divider in a closed position to create a seal between the first and second units.

2. The apparatus of claim 1, wherein the first unit is configured to receive a non-sterile medical device and the second unit is configured to receive a sterile medical device.

3. The apparatus of claim 1, further comprising:
a visual indicator associated with each of the first unit and the second unit, the visual indicators configured to indicate a state of the first medical device and the second medical device, respectively.

4. The apparatus of claim 3, wherein the state is selected from the group consisting of:
sterile and non-sterile.

5. The apparatus of claim 1, further comprising the supply kit and wherein the supply kit is disposable.

6. The apparatus of claim 5, wherein the supply kit comprises a paper box.

7. The apparatus of claim 1, further comprising the supply kit and wherein the supply kit is configured to receive a discarded material.

8. The apparatus of claim 1, further comprising the supply kit and wherein the supply kit includes at least one of a rag, a cloth, a paper product, a brush, a sponge, a spray device, a valve, and a fitting.

9. The apparatus of claim 1, wherein the first medical device is an endoscope.

10. A sterilization storage apparatus comprising:
a first unit comprising:
a first container having a first cavity configured to receive a first endoscope;
a second container having a second cavity configured to receive a supply kit for the endoscope, the second container is positioned proximal to the first container within the storage apparatus, wherein the supply kit includes at least one of a rag, a cloth, a paper product, a brush, a sponge, a spray device, a valve, and a fitting, wherein the first and second containers are formed from a single continuous material or have separate sidewalls that result in double-wall separation; and
a second unit comprising:
a third container having a third cavity configured to receive a second endoscope; and
a fourth container having a fourth cavity configured to receive a second supply kit for the second endoscope, the fourth container is positioned proximal to the third container within the storage apparatus;
a divider positioned between the first unit and the second unit, wherein the divider limits cross-contamination between the first and second units;
a visual indicator associated with each of the first and second units, the visual indicators configured to indicate a state of the first endoscope and the second endoscope, respectively; and
a door configured to enable access to both the first and second units and engage the divider in a closed position to create a seal between the first and second units.

* * * * *